United States Patent
Okada et al.

(10) Patent No.: US 6,265,633 B1
(45) Date of Patent: Jul. 24, 2001

(54) ISOLATED AND PURIFIED NUCLEIC ACIDS COMPRISING A GENE AND A REGULATORY REGION FOR THE GENE EXPRESSION OF THE SAME

(75) Inventors: Yukio Okada; Kazutoshi Ito, both of Gunma-ken (JP)

(73) Assignee: Sapporo Breweries Ltd., Tokyo (JP)

( * ) Notice: Subject to any disclaimer, the term of this patent is extended or adjusted under 35 U.S.C. 154(b) by 0 days.

(21) Appl. No.: 09/252,816

(22) Filed: Feb. 19, 1999

(30) Foreign Application Priority Data

Feb. 19, 1998 (JP) .................................................. 10-037266
Jun. 22, 1998 (JP) .................................................. 10-174235

(51) Int. Cl.[7] ........................... C12N 15/29; C12N 15/52; C12N 5/04; C12N 15/82; A01H 5/00
(52) U.S. Cl. ....................... 800/278; 435/320.1; 435/419; 435/468; 536/23.6; 800/298
(58) Field of Search .................................. 435/410, 419, 435/468, 69.1, 320.1; 536/23.6; 800/278, 295, 298

(56) References Cited

PUBLICATIONS

Sive et al, Nucl. Acids Res., vol. 16, No. 22, p. 10937, 1988.*
Likens et al, Crop Sci., vol. 18, pp. 380–386, 1978.*
Speirs et al, Meth. Plant Biochem., vol. 10, pp. 1–32, 1993.*
Sparvoli et al, Plant Mol. Biol., vol. 24, pp. 743–755, 1994.*
Suen–Ying Fung, et al., Phytochemistry, vol. 44, No. 6, pp. 1047–1053, "Conversion of Deoxyhumulone Into the Hop Alpha–Acid Humulone", Mar. 1997.
Karin W. M. Zuurbier, et al., Phytochemistry, vol. 38, No. 1, pp. 77–82, "Formation of Aromatic Intermediates in the Biosynthesis of Bitter Acids in *Humulus lupulus*", Jan. 1995.
Y. Okada, et al., EMBL Sequence Data Library, 2 pages, "A Chalcone Synthase–Like Gene Expressed Specifically in Lupulin Glands of Hop (*Humulus Lupulus*)", Jun. 23, 1998.
Norma B. Paniego, et al., European Journal of Biochemistry, vol. 262, pp. 612–616, "Phlorisovalerophenone Synthase, a Novel Polyketide Synthase From Hop (*Humulus Lupulus L.*) Cones", Jun. 1999.
Hiroyasu Tobe et al, "Bone Resorption Inhibitors From Hop Extract", Biosci. Biotech. Biochem., 61(1), pp. 158–159, 1997.
P.R. Sanders et al, "Comparison of Cauliflower Mosaic Virus 35S and Nopaline Synthase Promoters in Transgenic Plants", Nucleic Acids Research, 15(4), pp. 1543–1558, 1987.

* cited by examiner

*Primary Examiner*—Gary Benzion
*Assistant Examiner*—Ashwin Mehta
(74) *Attorney, Agent, or Firm*—Oblon, Spivak, McClelland, Maier & Neustadt, P.C.

(57) ABSTRACT

An isolated and purified nucleic acid comprising a gene specifically expressed in hop lupulin glands. Hops are dioecious, and only female plants bear cones, the lupulin glands of which contain secondary metabolic products which provide bitterness and flavor to beer. These secondary metabolic products contain some pharmacologically effective compounds. In order to breed a more useful cultivar of hops by manipulating the constituent of such useful secondary metabolic products relying on genetic engineering techniques, this invention provides an isolated and purified nucleic acid comprising a gene specifically expressed in hop lupulin glands. By using this nucleic acid, it is possible to develop a novel method for breeding hops with transformation techniques and molecular selection techniques. Furthermore, the present invention also provides a nucleic acid comprising the regulatory region for specifically expressing genes in lupulin glands. This nucleic acid can be used also for hop breeding.

7 Claims, 2 Drawing Sheets

SEQUENCE LISTING

```
<160> NUMBER OF SEQ ID NOS:  7

<210> SEQ ID NO 1
<211> LENGTH: 394
<212> TYPE: PRT
<213> ORGANISM: Humulus lupulus

<400> SEQUENCE: 1

Met Ala Ser Val Thr Val Glu Gln Ile Arg Lys Ala Gln Arg Ala Glu
  1               5                  10                  15

Gly Pro Ala Thr Ile Leu Ala Ile Gly Thr Ala Val Pro Ala Asn Cys
                 20                  25                  30

Phe Asn Gln Ala Asp Phe Pro Asp Tyr Tyr Phe Arg Val Thr Lys Ser
             35                  40                  45

Glu His Met Thr Asp Leu Lys Lys Lys Phe Gln Arg Met Cys Glu Lys
         50                  55                  60

Ser Thr Ile Lys Lys Arg Tyr Leu His Leu Thr Glu Glu His Leu Lys
 65                  70                  75                  80

Gln Asn Pro His Leu Cys Glu Tyr Asn Ala Pro Ser Leu Asn Thr Arg
                 85                  90                  95

Gln Asp Met Leu Val Val Glu Val Pro Lys Leu Gly Lys Glu Ala Ala
                100                 105                 110

Ile Asn Ala Ile Lys Glu Trp Gly Gln Pro Lys Ser Lys Ile Thr His
            115                 120                 125
```

```
Leu Ile Phe Cys Thr Gly Ser Ser Ile Asp Met Pro Gly Ala Asp Tyr
    130                 135                 140

Gln Cys Ala Lys Leu Leu Gly Leu Arg Pro Ser Val Lys Arg Val Met
145                 150                 155                 160

Leu Tyr Gln Leu Gly Cys Tyr Ala Gly Gly Lys Val Leu Arg Ile Ala
                165                 170                 175

Lys Asp Ile Ala Glu Asn Asn Lys Gly Ala Arg Val Leu Ile Val Cys
            180                 185                 190

Ser Glu Ile Thr Ala Cys Ile Phe Arg Gly Pro Ser Glu Lys His Leu
        195                 200                 205

Asp Cys Leu Val Gly Gln Ser Leu Phe Gly Asp Gly Ala Ser Ser Val
    210                 215                 220

Ile Val Gly Ala Asp Pro Asp Ala Ser Val Gly Glu Arg Pro Ile Phe
225                 230                 235                 240

Glu Leu Val Ser Ala Ala Gln Thr Ile Leu Pro Asn Ser Asp Gly Ala
                245                 250                 255

Ile Ala Gly His Val Thr Glu Ala Gly Leu Thr Phe His Leu Leu Arg
            260                 265                 270

Asp Val Pro Gly Leu Ile Ser Gln Asn Ile Glu Lys Ser Leu Ile Glu
        275                 280                 285

Ala Phe Thr Pro Ile Gly Ile Asn Asp Trp Asn Asn Ile Phe Trp Ile
    290                 295                 300

Ala His Pro Gly Gly Pro Ala Ile Leu Asp Glu Ile Glu Ala Lys Leu
305                 310                 315                 320

Glu Leu Lys Lys Glu Lys Met Lys Ala Ser Arg Glu Met Leu Ser Glu
                325                 330                 335

Tyr Gly Asn Met Ser Cys Ala Ser Val Phe Phe Ile Val Asp Glu Met
            340                 345                 350

Arg Lys Gln Ser Ser Lys Glu Gly Lys Ser Thr Thr Gly Asp Gly Leu
        355                 360                 365

Glu Trp Gly Ala Leu Phe Gly Phe Gly Pro Gly Leu Thr Val Glu Thr
    370                 375                 380

Val Val Leu His Ser Val Pro Thr Asn Val
385                 390

<210> SEQ ID NO 2
<211> LENGTH: 1359
<212> TYPE: DNA
<213> ORGANISM: Humulus lupulus

<400> SEQUENCE: 2
tttcacagta ctactagcta tatatatatc aggtaatggc gtccgtaact gtagagcaaa      60
tccgaaaggc tcagcgagct gaaggtccgg ccaccatcct cgccattggc accgccgttc     120
ctgccaactg tttcaaccaa gctgattttc ccgactacta ctttcgtgtc accaaaagtg     180
aacacatgac tgatctcaaa aagaagttcc aacgaatgtg tgaaaaatcc actataaaaa     240
agcgttactt gcacttgacc gaagagcatc tgaagcagaa cccacatctg tgcgagtaca     300
atgcaccatc tctgaacaca cgccaagaca tgttggtggt tgaagttccc aagcttggga     360
aggaggctgc aatcaatgcc atcaaagaat ggggccaacc caagtccaag atcacccatc     420
tcatcttctg caccggctcc tccatcgaca tgccaggagc cgattaccaa tgcgccaagc     480
ttctcggcct ccgaccctcg gtgaagcgag tgatgctgta tcaactcggc tgttatgccg     540
gtggaaaagt tcttcgcata gccaaggaca tagcagagaa caacaagggc gctagagttc     600
```

```
tcattgtgtg ctctgagatc acagcttgta tctttcgcgg gccctcggag aaacatttgg      660
attgcttggt ggggcaatct ctgttcggag acgggcatc ttcggtcatc gttggtgccg       720
accctgatgc ctcggtaggc gagcggccga tcttcgagtt ggtttcagct gcgcagacga     780
ttttgcctaa ctcggatgga gccatagccg ggcacgtaac ggaagccggg ctgacatttc     840
acttgctgag ggacgtgcca gggttgatct cccaaaacat tgagaagagc ttgattgagg     900
ccttcactcc gattgggatt aatgactgga caacatatt ctggattgca catcccggtg      960
gacctgccat tctggacgag atagaggcca agctcgagct gaagaaggag aagatgaagg     1020
cgtctcgtga aatgctgagc gagtatggga acatgtcatg tgcaagcgtt ttcttcatag     1080
tagatgagat gaggaaacag tcgtcgaagg aagggaagtc taccaccgga gatggactgg    1140 agtgggcgc tctcttcggg tttggaccgg gtctgacggt ggagacggtg gtcttgcaca     1200
gcgtgcccac aaacgtctaa tgaataattt gttatcgcta gcttgtcaaa tcaagcttta    1260
ctatgtattg tggtcgttaa ttagtttata ctttgatgtt gatcaataat tatataccct     1320
atctaataaa atgatcaaat atatttttat ataaaaaaa                            1359

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:
      polynucleotide

<400> SEQUENCE: 3
cgaaagtagt agtcgggaaa atcagcttgg                                       30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:
      polynucleotide

<400> SEQUENCE: 4
gcaccatctc tgaacacacg ccaagacatg                                       30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:
      polynucleotide

<400> SEQUENCE: 5
agcttggttg aaacagttgg caggaacggc                                       30

<210> SEQ ID NO 6
<211> LENGTH: 3439
<212> TYPE: DNA
<213> ORGANISM: Humulus lupulus

<400> SEQUENCE: 6
gcaccatctc tgaacacacg ccaagacatg ttggtggttg aagttcccaa gcttgggaag      60
gaggctgcaa tcaatgccat caaagaatgg ggccaaccca gtccaagat cacccatctc      120 atcttctgca ccggctcctc catcgacatg ccaggagccg attaccaatg cgccaagctt     180
```

-continued

```
ctcggcctcc gaccctcggt gaagcgagtg atgctgtatc aactcggctg ttatgccggt    240
ggaaaagttc ttcgcatagc caaggacata gcagagaaca acaagggcgc tagagttctc    300
attgtgtgct ctgagatcac agcttgtatc tttcgcgggc cctcggagaa acatttggat    360
tgcttggtgg ggcaatctct gttcggagac ggggcatctt cggtcatcgt tggtgccgac    420
cctgatgcct cggtaggcga gcggccgatc ttcgagttgg tttcagctgc gcagacgatt    480
ttgcctaact cggatggagc catagccggg cacgtaacgg aagccgggct gacatttcac    540
ttgctgaggg acgtgccagg gttgatctcc caaaacattg agaagagctt gattgaggcc    600
ttcactccga ttgggattaa tgactggaac aacatattct ggattgcaca tcccggtgga    660
cctgccattc tggacgagat agaggccaag ctcgaggagt tggagactg tccgaggtcc     720 ttctcctagg gtgatcacca gctcgatagt ccctatagcc gttgatcctt ctcccgaaaa    780
accgcacagc atcatggagg tcgccttcag ctcggcgaca gtcaaaccca tcttctccaa    840
cgtggaccgg aatagaaggt ttaccgagct cccattatcg atcaacaccc tcctaaccct    900
ccgaatagcg agctgaactg ctacgaccag agggtcgtta tgagggaact ggacatggcc    960
cgcatcttct tctgtaaaaa tgatcggttg cctctccaat cgctgctgct ttggcagacg   1020
ctgctccggg acgaactcta ctccattatg cgccttgagt tcgtttacgt atctcttttg   1080
ggcaccccta ctcacgctag ctaaatgcgg acctccagag attgtggata tctctcctcc   1140
aatcactgga ggagggacgt cttgatctat ccgagaccca gaaatctata caaaaaaaaa   1200
actatgtata aggttcataa acacattata ttcattaatt taaccttaaa attaaaaaaa   1260
atgaaaaaaa ctcaccaaaa ttggtctagg aagtcggaga cgccgctagt tcttgggaga   1320
aaacctaagt tttgaatttg ggagaatgaa gggcttgggg tcgatggctg agatttaata   1380
ctgggtgcac tgtttgcgtt agtgggcaac tgacgctaac ggcttgtttg catcagtgcc   1440
aaactgacgc aaacacaccg ttagcgttag ttgcccactg acgcaaacgg tgcattaaga   1500
gcatcagttg gccactgacg caaacttcac caattaacag tgtcagtgtt atcactgatg   1560
caaatgcccc tgaatttgtg gtagtactca acttccacaa atgctgattc tcggtcaacg   1620
gcgtcagtca actgtgttga gtgacgcgtt tgactgacac aaaataagta ttttggtgta   1680
gtggaagatt aactaagaag gtaaaattgg aggttattgt tatcactcct tcatcattta   1740
taaaagtaga aatacgttcc atttaatata ctaaccaacc ttgctgccac atatcccctg   1800
aaaaaaataa aacaacaaca acctttctac cataaaatta ggcatatgat gatatataac   1860
ctaactataa cacaaaatta ggcatatgat gatatatata acctaactat aacacaaaat   1920
taggcatata tatatacact cacaaatagt ggctgctata cccaacacct taattaatta   1980
atagttaatg ctcctctaga agactggacg agatcaagtg ctattatgcg gaatcaagat   2040
ctcctatcaa aaaagatgt cccagcctat gtttagaaaa tgttaaatca aattctgtta    2100
actaatttct atatttctca tccctactcc tttttttta acaatcaaca attcattgaa    2160
aataatcaaa atgtaataca actaataata agatgatata tatagtaact atccatacaa   2220
gttcattatc cactctaagt gcatgcacaa ttcatgaacg gccttattgg ccaaacgtca   2280
aacacaaatt agagatacct tagaaaaatt ggataataaa cttgttatat tttctaacaa   2340
agaccctaat tcattactac tccattaaat gacgtgtatc tttcattttt ttttaaaaat   2400
tttagaaact aatagagtat ggattgatgc tgcattataa gaaatcgatc acaccttcag   2460
ttatgaactt tccggctaag caccatcggg catctatgtc ctcctctttt gccacattat   2520
```

-continued

| | |
|---|---|
| catatgaaat accactgttt tcctcctctt ccaagcttat ggtcaagacc ggccctgaac | 2580 |
| taaggtgggt tagacccacg cctagggcct attttttttt acatttcttt taaaaatact | 2640 |
| ataaattttt aaaagtttt tacaaaaagg gccctaatc accaattttt cctaaggctc | 2700 |
| aaaactcttc agggccagcc ctgcctatgg tagcatatct agattctaaa tcttgcttat | 2760 |
| gagaactgct cgatgccata acttccttcg ccaccaagac taataacaca acaatagag | 2820 |
| aacgaacaca ccaatagcaa tacaaaacac cttacgtcaa ctgacccaac agagagctac | 2880 |
| catgtcaaaa gacaatacta gtttgagact tcaccactgt caaaattcta gttctcaaca | 2940 |
| ctagcaaaaa aaaaagtgtt aaacaccatc aatcacataa cgacatactt cttggccata | 3000 |
| tttttttttcc catgtaatca tgtaaaaggt ggggaaaata aatcaataca cataaagaac | 3060 |
| aatgaaaaaa taaataaaca agtcaaatta ttataattta acattaataa aaagttgaga | 3120 |
| atcacaaaca ttggtacgta ggtattaggg ttggtgttta cacatattat ccataggcca | 3180 |
| tgcacacctt acctaaccca tgcaccactt tgtacatatt atatatataa ctccaatttg | 3240 |
| gctttgcatt tcaacacttg taatcattac actatatttg tgtatatagt gtaagttttc | 3300 |
| acagtactac tagctatata tatatcaggt aatggcgtcc gtaactgtag agcaaatccg | 3360 |
| aaaggctcag cgagctgaag gtccggccac catcctcgcc attggcaccg ccgttcctgc | 3420 |
| caactgtttc aaccaagct | 3439 |

<210> SEQ ID NO 7
<211> LENGTH: 2606
<212> TYPE: DNA
<213> ORGANISM: Humulus lupulus

<400> SEQUENCE: 7

| | |
|---|---|
| ctcgaggagt ttggagactg tccgaggtcc ttctcctagg gtgatcacca gctcgatagt | 60 |
| ccctatagcc gttgatcctt ctcccgaaaa accgcacagc atcatggagg tcgccttcag | 120 |
| ctcggcgaca gtcaaaccca tcttctccaa cgtggaccgg aatagaaggt ttaccgagct | 180 |
| cccattatcg atcaacaccc tcctaaccct ccgaatagcg agctgaactg ctacgaccag | 240 |
| agggtcgtta tgagggaact ggacatggcc cgcatcttct tctgtaaaaa tgatcggttg | 300 |
| cctctccaat cgctgctgct ttggcagacg ctgctccggg acgaactcta ctccattatg | 360 |
| cgccttgagt tcgtttacgt atctcttttg ggcaccccta ctcacgctag ctaaatgcgg | 420 |
| acctccagag attgtggata tctctcctcc aatcactgga ggagggacgt cttgatctat | 480 |
| ccgagaccca gaaatctata caaaaaaaaa actatgtata aggttcataa acacattata | 540 |
| ttcattaatt taaccttaaa attaaaaaaa atgaaaaaaa ctcaccaaaa ttggtctagg | 600 |
| aagtcggaga cgccgctagt tcttgggaga aaacctaagt tttgaatttg ggagaatgaa | 660 |
| gggcttgggg tcgatggctg agatttaata ctgggtgcac tgtttgcgtt agtgggcaac | 720 |
| tgacgctaac ggcttgtttg catcagtgcc aaactgacgc aaacacaccg ttagcgttag | 780 |
| ttgcccactg acgcaaacgg tgcattaaga gcatcagttg gccactgacg caaacttcac | 840 |
| caattaacag tgtcagtgtt atcactgatg caaatgcccc tgaatttgtg gtagtactca | 900 |
| acttccacaa atgctgattc tcggtcaacg gcgtcagtca actgtgttga gtgacgcgtt | 960 |
| tgactgacac aaaataagta ttttggtgta gtggaagatt aactaagaag gtaaaattgg | 1020 |
| aggttattgt tatcactcct tcatcattta taaagtaga aatacgttcc atttaatata | 1080 |
| ctaaccaacc ttgctgccac atatcccctg aaaaaaataa aacaacaaca acctttctac | 1140 |
| cataaaatta ggcatatgat gatatataac ctaactataa cacaaaatta ggcatatgat | 1200 |

-continued

```
gatatatata acctaactat aacacaaaat taggcatata tatatacact cacaaatagt      1260
ggctgctata cccaacacct taattaatta atagttaatg ctcctctaga agactggacg      1320
agatcaagtg ctattatgcg gaatcaagat ctcctatcaa aaaaagatgt cccagcctat      1380
gtttagaaaa tgttaaatca aattctgtta actaatttct atatttctca tccctactcc      1440
ttttttttta acaatcaaca attcattgaa aataatcaaa atgtaataca actaataata      1500
agatgatata tatagtaact atccatacaa gttcattatc cactctaagt gcatgcacaa      1560
ttcatgaacg gccttattgg ccaaacgtca aacacaaatt agagatacct tagaaaaatt      1620
ggataataaa cttgttatat tttctaacaa agaccctaat tcattactac tccattaaat      1680
gacgtgtatc tttcattttt ttttaaaaat tttagaaact aatagagtat ggattgatgc      1740
tgcattataa gaaatcgatc acaccttcag ttatgaactt tccggctaag caccatcggg      1800
catctatgtc ctcctctttt gccacattat catatgaaat accactgttt tcctcctctt      1860
ccaagcttat ggtcaagacc ggccctgaac taaggtgggt tagacccacg cctagggcct      1920
attttttttt acatttcttt taaaaatact ataaattttt aaaagtttt tacaaaaagg       1980 gccctaatc accaatttt cctaaggctc aaaactcttc agggccagcc ctgcctatgg        2040
tagcatatct agattctaaa tcttgcttat gagaactgct cgatgccata acttccttcg      2100
ccaccaagac taataacaca aacaatagag aacgaacaca ccaatagcaa tacaaaacac      2160
cttacgtcaa ctgacccaac agagagctac catgtcaaaa gacaatacta gtttgagact      2220
tcaccactgt caaaattcta gttctcaaca ctagcaaaaa aaaaagtgtt aaacaccatc      2280
aatcacataa cgacatactt cttggccata tttttttcc catgtaatca tgtaaaaggt       2340
ggggaaaata aatcaataca cataaagaac aatgaaaaaa taaataaaca agtcaaatta     2400
ttataattta acattaataa aaagttgaga atcacaaaca ttggtacgta ggtattaggg      2460
ttggtgttta cacatattat ccataggcca tgcacacctt acctaaccca tgcaccactt      2520
tgtacatatt atatatataa ctccaatttg gctttgcatt tcaacacttg taatcattac      2580
actatatttg tgtatatagt gtaagt                                          2606
```

ISOLATED AND PURIFIED NUCLEIC ACIDS COMPRISING A GENE AND A REGULATORY REGION FOR THE GENE EXPRESSION OF THE SAME

BACKGROUND OF THE INVENTION

1. Field of the Invention

The present invention relates to nucleic acids comprising a gene specifically expressed in lupulin glands of hops and to regulatory sequences thereof.

2. Discussion of the Background

Plants produce and store a wide variety of low molecular weight organic compounds including terpenoids, alkaloids, phenolics, saponins, etc. Since, formerly, these compounds were not considered to be directly involved in supporting living matter having only minor biological functions, they were conventionally called "secondary metabolic products".

Now, however, it has been elucidated that these secondary metabolic products function for promoting cellular differentiation and protecting cells from external harmful factors, and, furthermore, these secondary metabolic products formed by plants have been utilized and applied in a wide field of popular foods, medicaments, dyes, etc.

These secondary metabolic products have been paid so much attention with respect to their usefulness that the production pathways thereof in plant cells have been successively elucidated, indicating that these compounds are produced via a complicated biosynthetic cascade involving a number of enzymes. Most of these compounds biosynthesized via a cascade of enzymatic reactions can be isolated by directly extracting plant materials, but such a direct extraction from plants not only does not meet the demand for production on a large scale, but also is generally expensive. Therefore, the development of methods for synthesizing these compound in vitro using cultured cells, etc. has been under way.

On the one hand, it has been elucidated that hops, a major material for rendering a refreshing bitterness and flavor to beer, secrete a variety of secondary metabolic products in lupulin glands on the cones, contributing a great deal to the bitterness and flavor of beer.

Based on these circumstances, hops have been subjected to various breeding attempts focused on secondary metabolic products accumulated in lupulin glands such as bitter substance, essential oils, etc. in addition to the improvement of their agricultural properties.

However, hops are a dioecious plant, and especially the male plant bears no cones, materials for beer, is not commercially appreciated, and accordingly has not been actively studied so that its genetic properties useful for beer brewing have hardly been elucidated at all. Therefore, at present, hop breeding by conventional crossing relies largely on breeders' experience and intuition, and no prediction can be made especially on the quality of fermentation products at all till the time of the actual bearing of cones.

On the other hand, these days, breeding methods using genetic engineering such as a transformation technique and marker assisted selection have become available for various plants. In these methods, a more objective breeding can be performed compared with those conventional breeding methods that largely depend on breeders' experience and intuition. The transformation technique is a technique for directly introducing a desired character by transferring and expressing a foreign gene in plant cells. The expression of a foreign gene can be performed by linking a desired structural gene and a terminator capable of functioning in plant cells to a gene expression regulating promoter which is capable of functioning also in plant cells, and transferring the resulting transformed promoter into plant cells. Promoters frequently used in experiments are exemplified by CaMV 35S capable of expressing a transferred gene in regardless of any tissues of relatively numerous varieties of plants, and the promoter for the nopaline synthetase gene (Sanders, P. R., et al., Nucleic Acid Res., 15 (1987) 1543–1558). Furthermore, in the practical aspect of genetic transformation, the transferred gene might be harmful for the plant growth, etc. Therefore, there has been also a demand for promoters capable of expressing a foreign gene in a desired tissue, desired period, and desired quantity. The advantage of the breeding method using the transformation technique over the conventional traditional breeding method is that the former method is capable of transducing a desired character to plants regardless of their species with a relatively high accuracy in a short time. Also in the case of hops, since they can be proliferated by root-planting, the procedure for fixing the transduced character is not required. Therefore, the breeding method using the transformation technique is especially effective for hops.

Marker assisted selection is an example of a breeding method using the DNA marker such as RFLP (Restriction Fragment Length Polymorphism) marker, and have been put into practical use, especially for rice and wheat. It has been generally agreed that transformation techniques are capable of transducing a character regulated by a single gene, but incapable of transducing a character regulated by multiple genes. Marker assisted selection is capable of compensating for these defects of transformation techniques.

A prerequisite for such a breeding method using gene technology is to elucidate genes related with the desired character and those regulating those genes. Especially, from the viewpoint of hops as the beer material as well as the source of effective drug ingredient, if genes related to the biosynthesis of secondary metabolic products secreted from lupulin glands contained in the cones of female plants are elucidated, these genes can be applied to the hop breeding method using the gene technology, and, furthermore, also to the field of medical treatment.

SUMMARY OF THE INVENTION

Therefore, in order to elucidate genes specifically expressed in lupulin glands and facilitate their practical application, it is an object of the present invention to isolate, purify and provide such genes, as well as regulatory sequences thereof, such as promoters, for these genes.

As described above, nucleic acids isolated and purified in the present invention comprise genes specifically expressed in the lupulin glands of hops, promoters specifically functioning in lupulin glands, and portions thereof.

Using these nucleic acids, the conventional method for breeding hops wholly dependent on the breeders experience and intuition can be converted to a more objective method using genetic engineering. As described above, since important secondary metabolic products, such as beer materials and effective drug ingredients, are secreted exclusively in lupulin glands on the hop cones, genes specifically expressed to function in lupulin glands are likely related to the biosynthesis of these secondary metabolic products. Thus, by utilizing genes capable of participating in the biosynthesis of secondary metabolic products as a marker, an improved marker assisted selection can be developed for the breeding of hops which will contribute significantly to the food and drug industries. In addition, by transferring the above-described genes to hops using a transformation technique, breeding of industrially useful cultivar can be accomplished. That is, by breeding hops using a genetic engineering technique with these nucleic acids, the composition of secondary metabolic products accumulating in lupulin glands can be regulated. Furthermore, the nucleic acids of the present invention enable the maintenance and improvement of hop quality for beer brewing, and the use of hops for drug production.

A more complete appreciation of the invention and many of the attendant advantages thereof will be readily obtained as the same becomes better understood by reference to the following detailed description when considered in connection with the accompanying drawings.

DETAILED DESCRIPTION OF THE INVENTION

By the above-described expression "specifically expressed" or "specifically functions," it is meant that the genes are expressed or functioning not only in lupulin glands alone but also doing so more in these glands as compared to other organs. That is, whether the genes are expressed or functioning "specifically" in lupulin glands or not can be determined by their expression amount and function intensity in lupulin glands compared with other organs.

Furthermore, by the expression "specifically expressed" or "specifically functions" it is not only meant that the genes are as specific as defined above throughout the entire developing period, etc. but also that the expression and function of the genes are more highly elevated by the specific developing period or external influences compared with other organs.

The above-described nucleic acids comprise both DNA and RNA. Also, the type of "genes" coded in the above-described nucleic acids includes any types such as genomic DNA, cDNA and mRNA.

Further, portions of the above-described nucleic acids are also included in the present invention. In some applications, even a partial sequence thereof alone is capable of functioning without a whole length thereof being required, i.e., use of a fragment having the desired functional property of the full-length sequence. For example, in the case of application of these nucleic acids to the breeding method by the marker assisted selection based on RFLP, molecules are identified by hybridization and PCR, wherein the size of probes and PCR primers used is sufficient if they comprise a portion of the above-described specific nucleic acids derived from lupulin glands, for example, a partial continuous sequence of several tens to several hundreds bp long.

Furthermore, in the present invention, the above-described genes specifically expressed in lupulin glands feature that the genes encode proteins related to the biosynthesis of secondary metabolic products generated in lupulin glands.

Proteins herein used include, for example, the amino acid sequence described in SEQ ID NO:1. Genes encoding the protein include those having the base sequence described in SEQ ID NO:2, and also those having the base sequence partially different from that of SEQ ID NO:2 but reserving the very base sequence encoding the above-described amino acid sequence. In the case of the use of this base sequence as probes and PCR primers, it can be modified to a certain extent so far as the resulting sequence retains the desired functional capability. All amino acid sequences encoding the above-described amino acid sequences are within the scope of the present invention. Specific nucleic acid sequences other than those described above are readily determined by using the well-established genetic code for codons which encode the amino acid residues of the proteins described above. The genetic code is set forth in L. Stryer, *Biochemistry*, Third Edition, 1988, W.H. Freeman and Co., incorporated herein by reference in its entirety.

Also, isolated and purified nucleic acids of the present invention comprise the gene encoding chalcone synthetase. This chalcone synthetase is the enzyme related to the metabolism of phenylalanine and tyrosine, and, more specifically, has been determined to catalyze the conversion of 1 mole of coumaroyl CoA and 3 moles of malonyl CoA to 4,2,4,6-tetrahydroxychalcone (naringenin-chalcone) in the biosynthesis of flavonoids. Therefore, the above-described nucleic acids can be used to regulate the metabolic system involved in the biosynthesis of flavonoids in plants, and also as a gene marker for characters related to flavonoids. Furthermore, recently, it has been indicated that a chalcone synthetase-like enzyme possibly has a valerophenone synthetase activity which catalyzes the biosynthesis of phlorisovalerophenone and phlorisobutyrophenone, the precursors of bitter substance, α-acid and β-acid (European Brewery Convention, Proceedings of the 26th Congress, p. 215 (1997)). These facts indicate that the protein encoded by the gene isolated in the present invention functions as the valerophenone synthetase participating in the biosynthesis of bitter substance. Accordingly, the above-described nucleic acids can be used for the regulation of the metabolic system concerning the biosynthesis of bitter substance in hops and also as the gene marker for the character related to bitter substance.

Nucleic acids isolated and purified in the present invention also include a regulatory sequence for the specific expression of the gene in lupulin glands, and the sequence contains a promoter which is activated in lupulin glands. Such a sequence includes, for example, one having the base sequence described in SEQ ID NO:7. This regulatory sequence specific in lupulin glands can be used to facilitate the expression of genes linked downstream thereof in lupulin glands.

Furthermore, it is an object of the present invention to provide a vector containing a gene specifically expressed in lupulin glands or a regulatory sequence specifically regulating the expression of gene in lupulin glands.

Breeding of plants such as hops can be achieved by transforming plants including hops using a vector bearing a gene specifically expressible in the above-described lupulin glands. Especially, such a vector becomes effective for the breeding by the elevation/suppression of the production of secondary metabolic products. Furthermore, this vector can be used not only for the plant breeding but also the production of secondary metabolic products by expressing the gene related to the biosynthesis the secondary metabolic products in cultured cells. If the production of secondary metabolic products becomes possible in cultured cells, the isolation of the secondary metabolic products can be easily performed.

Also, the above-described vector bearing a regulatory sequence can be used not only for the expression of the specific genes but also for the specific expression of a desired gene in hop lupulin glands by linking a gene derived from hops or different plant species downstream of the regulatory sequence. By doing so, any desired gene in lupulin glands can be expressed.

In addition, the present invention also includes plant cells transformed by the above-described vector. Herein, plant cells can include, without any limitations in their morphology or growing stages, various types of cells such as cultured cells, callus, protoplasts, plant, etc. This invention can also include not only plant cells of the first generation but also plants generated from the first generation plant cells.

The above-described transformed plant enables the expression of desired genes including those encoding secondary metabolic products by the transfer of the above-described vector, increasing the usefulness of plants as materials for foods and drugs.

In the following description, the present invention will be described in detail with reference to preferred embodiments.

1. Isolation of nucleic acids comprising hop lupulin gland-specific gene and the expression regulatory sequence thereof (1) Preparation of Total RNA and mRNA Total RNA can be prepared by the existing method, for example, a method described in "Protocols of Plant PCR Experiment", Shujun-sha, p. 56 (1995), incorporated herein by reference. The preparation of mRNA from the total RNA can be carried out by the existing method, for example, according to the protocol attached to "Oligotex-dT30 <Super>" available from Takara-Shuzo.

(2) Preparation of cDNA Library cDNA library can be prepared from mRNA by the existing method. cDNA can be prepared, for example, according to the protocol attached to "cDNA synthesis module", Amersham. Also, the formation of a library of cDNA thus prepared can be performed according to protocols attached to "cDNA rapid adaptor ligation module" and "cDNA rapid cloning module" both from Amersham, and "GIGAPACK II Plus Packaging Extract", Stratogene. All of the above-cited publications are incorporated herein by reference.

(3) Preparation of Lupulin-specific Probes

By lupulin-specific probes is meant gene fragments complementary to genes specifically expressed in lupulin glands. In the present preferred embodiment, the lupulin-specific probes can be obtained by the following method.

Cones approximately 15 days after blooming are divided into a fraction comprising mainly lupulin glands and the bracteole base dense with lupulin glands (lupulin-rich fraction) and a fraction comprising mainly the stipular bract containing few lupulin glands (lupulin-poor fraction), respectively. A group of genes expressed in the lupulin-rich fraction has subtracted from it a group of genes also expressed in the lupulin-poor fraction, and a group of remaining genes are considered to be the ones specifically expressed in lupulin glands with a high probability.

Such a subtraction of a group of genes expressed also in the lupulin-poor fraction from a group of genes expressed in the lupulin-rich fraction can be carried out by the existing method, conveniently, for example, according to the protocol attached to a "Subtractor Kit" from Invitrogen.

(4) Isolation of Lupulin-specific cDNA

By "lupulin-specific cDNA" is meant cDNA derived from the gene specifically expressed in lupulin glands. Isolation of lupulin-specific cDNA can be performed by screening cDNA library prepared from the lupulin-rich fraction using the lupulin-specific probes. This screening can be carried out by the existing method, for example, by a method described in the "User's guide for performing the hybridization using DIG system" (Boehringer Mannheim, p. 37 (1995)), incorporated herein by reference.

Labeling of lupulin-specific probes can be also carried out by the existing method, for example, according to the protocol attached to "DIG-High Prime", Boehringer Mannheim.

(5) Preparation of Hop Genomic DNA

Preparation of hop genomic DNA can be performed by the existing method, for example, a method described in "Protocols for plant PCR experiment" (Shu-jun Sha, p. 54 (1995)), incorporated herein by reference.

(6) Isolation of Nucleic Acid Comprising a Regulatory Region for the Lupulin-specific Gene Expression By "nucleic acid comprising a regulatory region for the lupulin-specific gene expression" is meant nucleic acid comprising a regulatory region containing the promoter specifically functioning in lupulin glands. The nucleic acid can be isolated by the existing method using the reverse PCR with the DNA sequence of lupulin-specific cDNA as the primer, for example, methods described in "Protocols for plant PCR experiment" (Shu-jun Sha, p. 69 (1995)), incorporated herein by reference.

(7) DNA Sequencing

DNA sequence thus isolated can be determined by the existing method, for example, according to the protocol attached to an "ABI PRISM Dye Primer Cycle Sequencing Ready Reaction Mt" (Perkin-Elmer), incorporated herein by reference. The DNA sequence thus decided can be examined for the homology to that of existing genes in other plant species.

(8) Northern Hybridization Analysis (hereinafter referred to as Northern analysis)

Whether the lupulin-specific gene thus isolated is actually expressed specifically in lupulin glands and whether the nucleic acid thus isolated comprising the lupulin-specific expression regulatory region regulating the gene actually functions specifically in lupulin glands can be confirmed by carrying out Northern analysis with the isolated lupulin-specific gene as the probe. Northern analysis can be performed by the existing method, for example, based on the methods described in "Protocols for non-isotope experiments-DIG hybridization (Shu-Jun Sha, p. 45 (1994)) and "User's guide for performing the hybridization using DIG system" (Boehringer Mannheim, p. 40 (1995)), both incorporated herein by reference.

2. Preparation of Vectors Bearing the Above-isolated Lupulin-specific Gene or Lupulin-specific Expression Regulatory Sequence Lupulin-specific gene the specificity of which in lupulin glands has been confirmed as described above can be expressed, according to the existing method, by inserting the gene downstream of the expression regulatory sequence in a suitable vector bearing the expression regulatory sequence followed by transferring the transformed vector to appropriate cells. There are no limitations on the type of vectors bearing the expression regulatory sequence, and a vector described below bearing lupulin-specific expression regulatory sequence and a commercially available expression vector (for example, pBI121 (CLONTECH) can be used.

Also, the construction of vector bearing the lupulin-specific expression regulatory sequence can be similarly achieved by selecting an appropriate vector from existing plasmids according to the purpose and inserting the above-described expression regulatory sequence, for example, SEQ ID NO:7 to it. In this case, the cloning region having various restriction sites for linking structural genes may be optionally included downstream of the expression regulatory sequence.

3. Applications

Since secondary metabolic products are abundantly secreted in hop lupulin glands, the lupulin-specific genes isolated above are highly likely to be the gene related to the biosynthesis of the secondary metabolic products. Therefore, the application of genes obtained above to the transformation technique and marker assisted selection enables, for example, hop breeding based on the improvement of secondary metabolic products formed in lupulin glands. For the above-described transformation technique, well-known methods can be used.

Having generally described this invention, a further understanding can be obtained by reference to certain specific examples which are provided herein for purposes of illustration only and are not intended to be limiting unless otherwise specified.

EXAMPLES

Example 1
Preparation of Lupulin-rich and Lupulin-poor Fractions

Hop cones were harvested 15 days after blooming, and frozen in liquid nitrogen. These frozen cones were dissected on dry-ice, and divided using a dissection forceps into a fraction comprising mainly lupulin glands and the endocyte base with dense lupulin glands, and a fraction comprising mainly the endocyst with few lupulin glands. These fractions were referred to as the lupulin-rich fraction and lupulin-poor fraction, respectively, and stored at −80° C.

Example 2
Preparation of Total RNA and mRNA from Lupulin-rich and Lupulin-poor Fractions Total RNA and mRNA of lupulin-rich fraction and lupulin-poor fraction were prepared as follows. Each fraction was frozen and pulferized in liquid nitrogen, suspended in a 2% CTAB solution (consisting of 2% cetyltrimethylammonium bromide, 0.1 M Tris (pH 9.5), 20 mM EDTA, 1.4 M NaCl and 1% β-mercaptoethanol), and incubated at 65 for 30 min. After the suspension was extracted twice with chloroform/isoamyl alcohol (24:1), a three quarters volume of isopropanol was added to the extract to precipitate DNA and RNA. After DNA and RNA thus precipitated were dissolved in water, a ⅓ volume of 10 M lithium chloride was added, and the resulting mixture was allowed to stand at −20° C. overnight, and then centrifuged at 15,000 rpm for 10 min. Precipitates thus obtained were washed with 70% ethanol and dissolved in a DNase reaction buffer (consisting of 100 mM sodium acetate (pH 5.2) and 5 mM magnesium chloride). To this mixture was added DNase, and the resulting mixture was incubated at 37° C. to decompose DNA. To the incubation mixture was added a ⅓ volume of 10 M lithium chloride, and the mixture was allowed to stand at −20° C. overnight, then centrifuged at 15,000 rpm for 10 min. Precipitates thus obtained were dissolved in water, and the resulting solution was purified by the extraction with phenol-chloroform, and subjected to the ethanol precipitation. Precipitates thus obtained were dissolved in water and used as the total RNA preparation, from which mRNA was prepared using an "Oligotex-dt30<Super>" (Takara-Shuzo) according to the protocol attached thereto.

Example 3
Preparation of Lupulin-specific Probes

Herein, lupulin-specific probes were prepared by subtracting mRNA present also in the lupulin-poor fraction from mRNA in the lupulin-rich fraction. More specifically, the lupulin-specific probes were prepared using a "Subtractor Kit" (Invitrogen) and according to the protocol attached to the Kit.

First, cDNA was synthesized from mRNA of the lupulin-rich fraction. Also, mRNA in the lupulin-poor fraction was labelled with biotin. Then, cDNA of the lupulin-rich fraction thus prepared was mixed with the biotinized mRNA in the lupulin-poor fraction to form a hybrid, to which was then added streptoavidin to combine with the biotinized mRNA in the hybrid. Then, the removal of the biotinized mRNA by extracting the hybrid with phenol-chloroform resulted in the depletion of cDNA derived from mRNA present also in the lupulin-poor fraction from the cDNA of the lupulin-rich fraction. As a result, cDNA derived only from the lupulin-rich fraction was obtained to be used as the probe. Lupulin-specific probes thus obtained were labelled with digoxigenin using a "DIG-High Prime" (Boehringer Mannheim).

Example 4
Isolation of Lupulin-specific cDNA

A cDNA library was prepared from mRNA in the lupuln-rich fraction using a "cDNA synthesis module", "cDNA rapid adaptor ligation module" and "cDNA rapid cloning module—MOSSlox" (Amersham), and "GIGAPACK Plus Packaging Extract" (Stratagene) with—MOSSlox as the vector. This library was screened by the hybridization method using lupulin-specific probes labelled with digoxigenin.

More specifically, each plaque derived from the above-described cDNA library was transferred to membrane filter, and blocked in a hybridization buffer (containing 5×SSC, 100 mM phosphate buffer, 7% SDS, 2% blocking agent, 0.1% N-lauroyl sarcosine, 50% formamide and 50 g/ml fish sp erm DNA). Then, to the hybridization buffer was added the above-described probe, and the membrane was incubated in the resulting mixture at 42° C. overnight. Then, the membrane was washed twice with a rinsing solution (containing 1% SDS and 2×SSC) at 56° C. for 5 min, and further twice with a rinsing solution (containing 0.1% SDS and 0.1×SSC) at 68° C. for 5 min. Then, by detecting the positive plaque, the lupuhin-specific cDNA was isolated.

Example 5
Determination of DNA Sequence of Lupulin-specific cDNA and Amino Acid Sequence of Translation Products The DNA sequence of gene fragments containing the lupuin-specific cDNA and lupuln-specific promoter thus obtained was then determined. For sequencing, each gene fragment was subcloned into the pUC vector or pBluescript vector. Sequencing was performed using a "ABI PRISM Dye Primer Cycle Sequencing Ready Reaction Kit" and a DNA sequencer (ABI373S model) (Perkin-Elmer).

The DNA sequence of the lupulin-specific cDNA thus determined is shown in SEQ ID NO:2. Also, the putative amino acid sequence of the translation product derived from the DNA sequencer is shown in SEQ ID NO:1. In this case, the amino acid sequence of SEQ ID NO:1 corresponds to the DNA sequence from the initiation codon (ATG), position 36–38 to the termination codon (TAA), position 1218–1220 in SEQ ID NO:2.

Example 6
Preparation of Hop Genomic DNA

Hop genomic DNA was prepared as follows. Leaves or cones of hops were frozen and pulferized in liquid nitrogen, suspended in a 2% CTAB solution (containing 2% cetyltrimethylammonium bromide, 0.1 M Tris (pH 9.5), 20 mM EDTA, 1.4 M NaCl and 1% β-mercaptoethanol), and incubated at 65° C. for 30 min. The suspension was extracted twice with chloroform-isoamylalcohol (24:1), and added with a ¾ volume of isopropanol to precipitate DNA and RNA. DNA and RNA thus precipitated were dissolved in a high salt TE buffer (containing 1 M NaCl, 10 mM Tris (pH 8.0) and 1 mM EDTA), added with RNase, and the mixture was incubated at 60" C. to decompose RNA. To the reaction mixture was added 2 volumes of isopropanol to precipitate DNA, which was washed with 70% ethanol, and then dissolved in water to obtain a genomic DNA sample.

Figure 1:
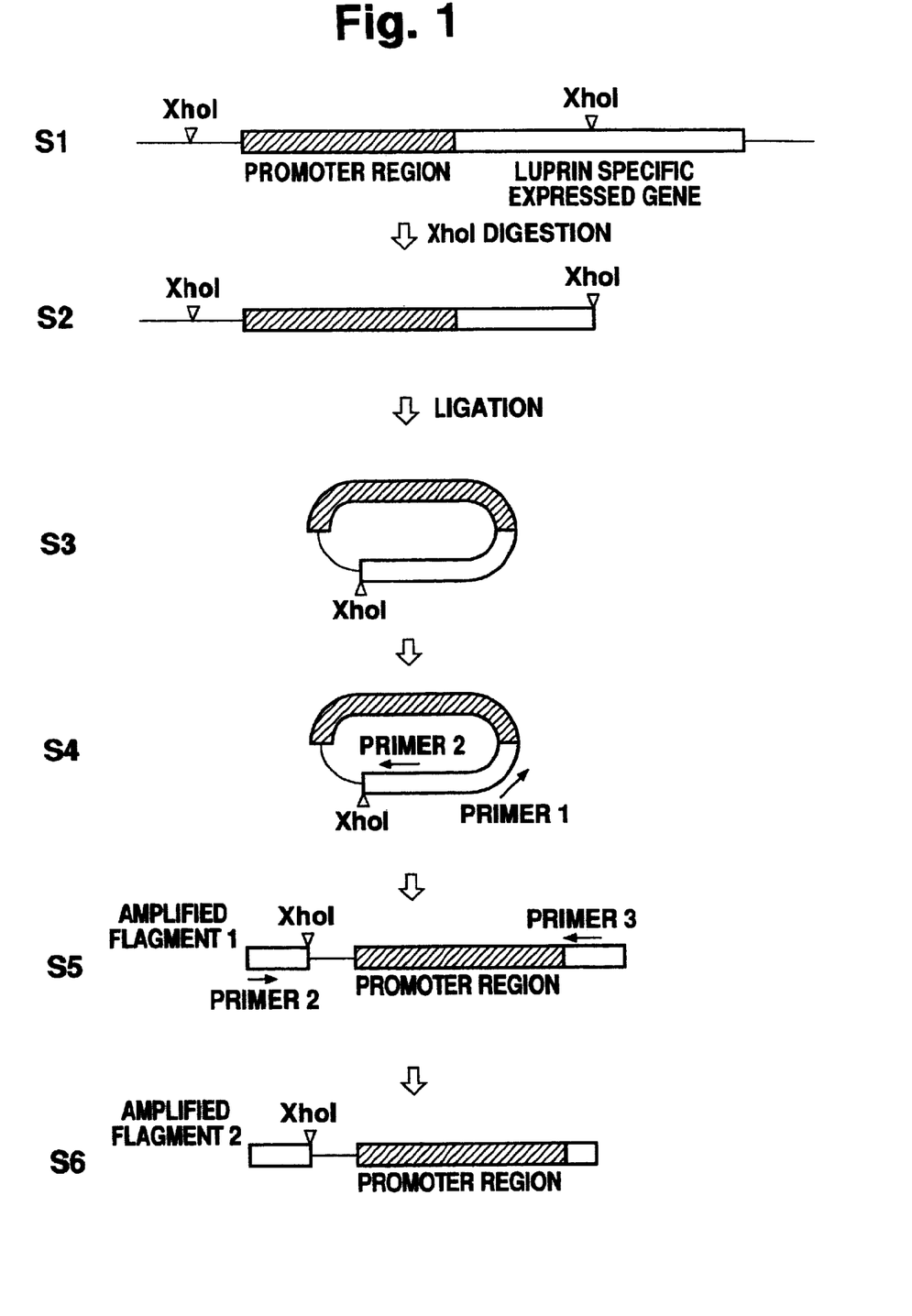
FIG. 1: diagram representing the procedure of inverse PCR in the case of isolation of the regulatory sequence in the lupulin-specific gene.

Example 7
Isolation of the Expression Regulatory Sequence for the Lupulin-specific Gene Isolation of the expression regulatory sequence for the lupulin-specific gene was carried out using the inverse PCR method as follows. FIG. 1 is a diagram representing the procedures in this Example 7.

First, hop genomic DNA obtained in Example 6 was digested with a restriction enzyme Xho I (S1 and S2). Xho I digests were subjected to self circularization according to the protocol attached to a "DNA Ligation Kit Ver. 1" (Takara-Shuzo) (S3).

Next, the flanking region containing the promoter for lupuin-specific gene was amplified by PCR using primers having the sequence within the lupulin-specific cDNA with a portion of this ligation reaction mixture as the template (S4). Sequences of a pair of primers herein used are represented in SEQ ID NO:3 (primer 1) and NO:4 (primer 2). Herein, SEQ ID NO:3 is a sequence complementary to that from position 137 to 166 and SEQ ID NO:4 is a sequence from position 303 to 332 of SEQ ID NO:2, respectively.

The above-described PCR was performed using an "Expand High-Fidelity PCR System" (Boehringer-Mannheim) according to the protocol attached thereto, incorporated herein by reference. The reaction conditions were as follows: after 30 cycles of the incubations at 94° C. for 1 min, 55° C. for 1 min and 68° C. for 4 min, the mixture was further incubated at 72° C. for 6 min.

The reaction solution thus obtained was electrophoresed for the identification of PCR products. Since, in addition to the amplified fragment 1, non-specific amplified fragments might be contained in the above PCR products, a selective amplification of only the desired fragment was further attempted using different primers (S5). That is, in order to selectively amplify only DNA segment comprising the lupulin-specific promoter, PCR was performed with a portion of the above-described PCR solution as the template using primer 3 (SEQ ID NO:5) complementary to the sequence further upstream of the lupulin-specific gene than primer 1 and the above-described primer 2 (S6). The primer 3 (SEQ ID NO:5) comprises the sequence complementary to that from Nos. 114 to 143 of the lupulin-specific cDNA (SEQ ID NO:2). PCR was carried out using the same conditions and apparatus as described above. Then, the DNA sequence was determined using the PCR-amplified fragment obtained using these primers 2 and 3.

Example 8
DNA Sequence Determination of the Expression Regulatory Sequence for the Lupulin-specific Gene Base sequence of the above-described amplified fragment 2 was determined similarly as in Example 5 described above by subeloning the amplified fragment to the pUC vector or pBluescript vector and using an ABI PRISM Dye Primer Cycle Sequencing Ready Reaction Kit and a DNA sequencer (ABI373S type) (Perkin-Elmer). Results are shown in SEQ ID NO:6.

Since this amplified fragment was obtained by the inverse PCR method, it is expected that the amplified fragment contains the expression regulatory sequence such as that of the promoter within the lupulin-specific gene (a portion thereof) Therefore, in order to identify this expression regulatory sequence, the DNA fragment thus amplified was compared with DNA sequence of the lupulin-specific cDNA. These comparisons revealed that the DNA fragment herein amplified (SEQ ID NO:6) contained the promoter sequence in the lupulin-specific cDNA. More specifically, the sequence position 1–690 of SEQ ID NO:6 corresponded to the sequence position 303–992 of the lupulin-specific cDNA (SEQ ID NO:2), and the sequence position 3296–3438 of SEQ ID NO:6 corresponded to the sequence Nos. 1–143 of the lupulin-specific cDNA (SEQ ID NO:2), respectively. Therefore, it has been indicated that the expression regulatory region such as the promoter for the lupulin-specific gene is included in the region position 691–3295 of SEQ ID NO:6, which is shown in SEQ ID NO:7.

Example 9
Northern Blot Analysis of the Lupulin-specific cDNA and the Expression Regulatory Sequence of the Lupulin-specific Gene Whether the above-described lupulin-specific cDNA was actually expressed in lupulin glands and whether the promoter for the above-described lupulin-specific gene actually functioned in lupulin glands were examined by the Northern blot analysis for the total RNAs extracted from the lupulin-rich and lupulin-poor fractions, respectively, using labelled DNAs prepared based on the lupulin-specific cDNA (SEQ ID NO:2) in Example 5.

First, the total RNAs from the lupulin-rich and lupulin-poor fractions were prepared by a similar method as in Example 2, and fractionated by denaturing agarose gel electrophoresis (1% agarose, 18% formaldehyde, 20 mM MOPS, 5 mM sodium acetate and 1 mM EDTA (pH 7)). RNAs thus fractionated in the agarose gel were transferred to nylon membrane, and subjected to hybridization using cDNA obtained above as the probe according to the Users guide for hybridization with DIG System (Boehringer-Mannheim, p.40 (1995)), incorporated herein by reference.

Hybridization was performed under the following conditions. The above-described membrane was blocked using a hybridization buffer of the same constituents as in Example 4. To the above-described hybridization buffer was added the lupulin-specific cDNA labelled with digoxigenin as the probe, the blocked membrane was soaked into this mixture, and incubated at 50° C. overnight. Then, the membrane was rinsed twice at 56° C. for 10 min with a washing solution (containing 1% SDS and 2×SSC), further twice at 68° C. for 30 min with a washing solution (containing 0.1% SDS and 0.1×SSC), and then searched for bands fused with the probe. Results are shown in FIG. 2.

Figure 2:
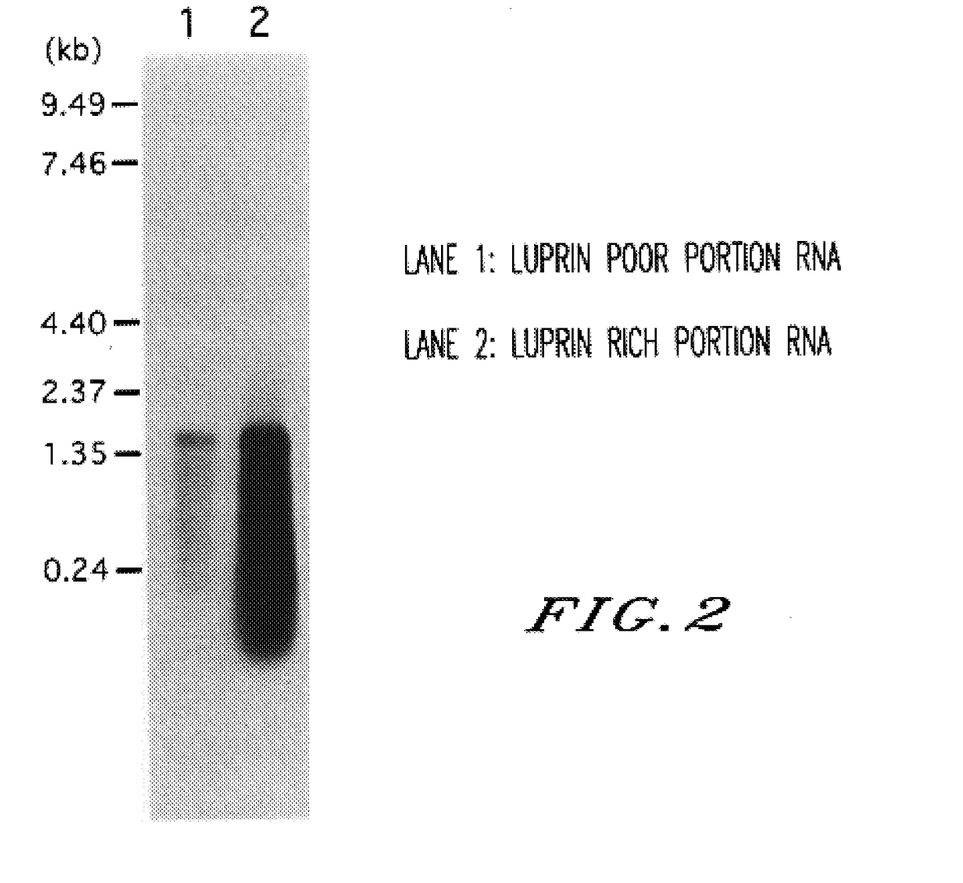
FIG. 2: results of Northern blot analysis of RNAs which have been recovered from lupulin-rich fraction and lupulin-poor fraction and electrophoresed using a lupulin-specific gene as the probe. The analytical results indicate the specificity of lupulin-specific gene expression in lupulin glands.

As represented in FIG. 2, although a few mRNAs for the gene obtained above were also present in the lupulin-poor fraction, they were clearly present in abundance in the lupulin-rich fraction, indicating the strong expression of this gene specifically in lupulin glands. The expression of this gene is controlled by the nucleic acid comprising the expression regulatory region containing the promoter localized upstream of the structural gene in the genomic DNA, and the nucleic acid comprising the expression regulatory region is the one isolated and identified in the above-described example, indicating a specifically strong function of the above-described isolated nucleic acid comprising the expression regulatory region in lupulin glands. Signal bands detected in the low molecular side were thought to be decomposed products of mRNA of the gene obtained above.

Example 10

Homology Examination

The putative amino acid sequence derived from the DNA sequence of the lupulin-specific cDNA thus obtained was compared for homology with the existing amino acid sequences. As a result, the gene had a high homology with the gene for chalcone synthetase catalyzing the synthesis of nalingenin concerned to the biosynthesis of flavonoids in plants. More specifically, in comparison with chalcon synthetases from other plants such as Arabidopsis (Plant J., 8 (5), 659–671 (1995)), barley (lant Mol. Biol. 16:1103–1106 (1991)), pea (EMBL/GenBank/DDBJ databases X80007), petunia (J. Biotechnol., 11 (2), 131–135 (1995) and rye (EMBL/GenBank/DDBJ databases X92547), the hop enzyme showed 65–70% homology in the DNA level and 70–75% homology in the amino acid level.

Recently, chalcone synthetase has been indicated to have the activity of valerophenone synthetase catalyzing phlorisovalerophenone and phlorisobutylophenone, precursors of bitter substance, α-acid and β-acid (European Brewery Convention, Proceedings of the 26th Congress, p. 215 (1997)), indicating a possibility for the translation product of the gene obtained above to participate in the biosynthesis of bitter substance as valerophenone synthetase.

Therefore, in the event that the gene specifically expressed in lupulin glands encodes chalcone synthetase, this nucleic acid can be used for improving flavonoids in plants. Also, in the case that this gene encodes valerophenone synthetase, this nucleic acid can be used for improving bitter substance in hops. Furthermore, since hop bitter substance, α-acid and β-acid, have pharmacological activity (Biosci. Biotech. Biochem. 61 (1), 158 (1997)), it is possible for the above-described nucleic acid to be applied to drug production.

Industrial Applicability

As described above, nucleic acids comprising genes specifically expressed in hop lupulin glands enable the breeding of hops by genetic engineering techniques focused on secondary metabolic products expressed in lupulin glands. Also, in the case of the use of vectors bearing the above-described lupulin-specific genes, it is expected that the production of secondary metabolic products can be achieved outside of plants, such as in cultured cells. Since such secondary metabolic products include important materials such as foods and drugs, and also since chalcone synthetase is involved in the biosynthesis of flavonoids, and valerophenone synthetase is involved in the biosynthesis of bitter substance, the present invention is expected to greatly contribute to the development and improvement of materials for foods and medicines.

Furthermore, the lupulin-specific promoter in the present invention can be utilized for the improvement of secondary metabolic products such as essential oil constituents and bitter substance accumulated in lupulin glands by inserting the gene of interest downstream of the promoter. The promoter can also be used for introducing novel other characters to hops.

Obviously, numerous modifications and variations of the present invention are possible in light of the above teachings. It is therefore to be understood that within the scope of the appended claims, the invention may be practiced otherwise than as specifically described herein.

This application is based on Japanese Patent Application Serial No. Hei 10-37266, filed on filed on Feb. 19, 1998, and Japanese Patent Application Serial No. Hei 10-174235, filed on filed on Jun. 22, 1998, both of which are incorporated herein by reference in their entirety.

---

What is claimed is:

1. An isolated and purified nucleic acid encoding a gene specifically expressed in hop lupulin glands, said nucleic acid selected from the group consisting of:
   (a) a nucleic acid comprising the nucleotide sequence of SEQ ID NO: 2;
   (b) a nucleic acid comprising a nucleic acid sequence which hybridizes to the nucleic acid of (a), wherein the hybridization conditions are at least as stringent as the following: hybridization in 5×SSC at 42° C. followed by washing once in 2×SSC at 56° C. and then washing twice in 0.1×SSC at 68° C.; wherein said nucleic acid sequence encodes a protein with the biological activity of a chalcone synthetase and a valerophenone synthetase;
   (c) a nucleic acid encoding the amino acid sequence of SEQ ID NO: 1;
   (d) a nucleic acid comprising a nucleic acid sequence which hybridizes to a nucleic acid of (c), wherein the hybridization conditions are at least as stringent as the following: hybridization in 5×SSC at 42° C. followed by washing once in 2×SSC at 56° C. and then washing twice in 0.1×SSC at 68° C.; wherein said nucleic acid sequence encodes a protein with the biological activity of a chalcone synthetase and a valerophenone synthetase; and
   (e) a nucleic acid that is complementary to (a), (b), (c), or (d).

2. A nucleic acid according to claim 1, wherein the gene encodes at least one protein involved in the biosynthesis of a secondary metabolic product.

3. The nucleic acid according to claim 2, wherein the nucleic acid encodes a protein having the biological activity of a chalcone synthetase and a valerophenone synthetase.

4. A vector comprising a nucleic acid of claim 1.

5. A plant cell transformed by the vector of claim 4.

6. A method of producing a transformed plant cell, comprising transforming a plant cell with the vector of claim 4.

7. A plant cell according to claim 5 wherein the plant cell is a hop plant cell.

* * * * *